United States Patent [19]

Andree et al.

[11] Patent Number: 5,186,734
[45] Date of Patent: Feb. 16, 1993

[54] HERBICIDAL BISAZINYL COMPOUNDS

[75] Inventors: Roland Andree; Mark W. Drewes, both of Langenfeld; Hans-Joachim Santel, Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[21] Appl. No.: 757,860

[22] Filed: Sep. 11, 1991

[30] Foreign Application Priority Data

Sep. 22, 1990 [DE] Fed. Rep. of Germany ....... 4030041

[51] Int. Cl.$^5$ .................... A01N 43/48; A01N 43/64; C07D 251/00; C07D 251/40
[52] U.S. Cl. .................................. 504/196; 504/197; 504/225; 504/230; 504/243; 504/239; 504/242; 504/165; 504/168; 544/194; 544/216; 544/217; 544/218
[58] Field of Search ...................... 71/92, 93; 544/296, 544/194, 216, 217, 218

[56] References Cited

U.S. PATENT DOCUMENTS 4,248,619  2/1981  Serban et al. ............................. 71/92
4,906,285  3/1990  Wada et al. ............................... 71/92
5,059,681 10/1991  Taylor .................................... 534/634

FOREIGN PATENT DOCUMENTS 0321846  6/1989  European Pat. Off. .
0336494 10/1989  European Pat. Off. .
1585950  3/1981  United Kingdom .

Primary Examiner—Nicholas S. Rizzo
Assistant Examiner—Matthew V. Grummbling
Attorney, Agent, or Firm—Sprung Horn Kramer & Woods

[57] ABSTRACT

Herbicidal bisazinyl compounds of the formula

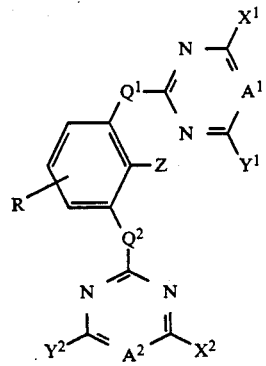

(I)

in which
A$^1$ and A$^2$ are identical or different and represent nitrogen or a C—X group, X representing hydrogen, halogen, alkyl or alkoxy, and
Q$^1$ and Q$^2$ are identical or different and represent oxygen, sulphur, NH or N-alkyl, (the substituents R, X$^1$, X$^2$, Y$^1$, Y$^2$ and Z representing a variety of organic radicals).

The compounds of the formulas

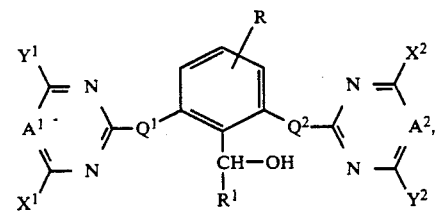

(II)

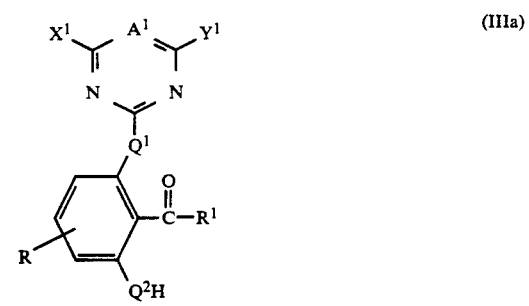

(IIIa)

and

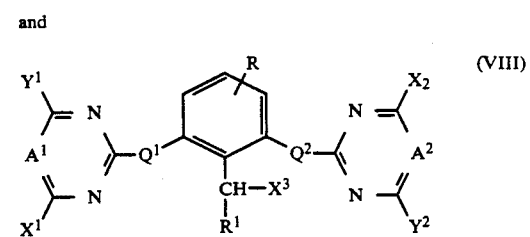

(VIII)

are also new.

9 Claims, No Drawings

HERBICIDAL BISAZINYL COMPOUNDS

The invention relates to new bisazinyl compounds, to a plurality of processes and new intermediates for their preparation, and to their use as herbicides.

It has already been disclosed that certain bisazinyl compounds have herbicidal properties (cf. EP-A 008,192, EP-A 321,846 and EP 336,494). However, compounds of the publications mentioned have not gained substantial importance to date.

The new bisazinyl compounds of the general formula (I) have now been found,

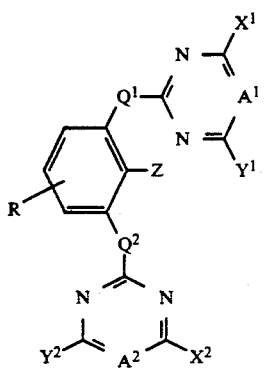

in which $A^1$ and $A^2$ are identical or different and represent nitrogen or a C—X group, X representing hydrogen, halogen, alkyl or alkoxy, $Q^1$ and $Q^2$ are identical or different and represent oxygen, sulphur, NH or N-alkyl, R represents hydrogen, amino, hydroxyl, cyano, nitro, halogen, alkyl, halogenoalkyl, alkoxy, halogenoalkoxy, alkylthio, halogenoalkylthio, alkylamino, dialkylamino, alkylcarbonylamino, alkoxycarbonylamino or alkylsulphonylamino, $X^1$, $X^2$, $Y^1$ and $Y^2$ are identical or different and represent hydrogen, halogen, alkyl, halogenoalkyl, alkoxy, halogenoalkoxy, alkylthio, alkylamino, dialkylamino or optionally substituted phenoxy, and Z represents one of the groups below:

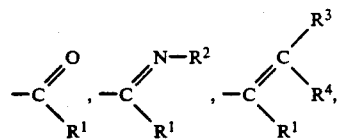

where $R^1$ represents hydrogen, optionally substituted alkyl or optionally substituted phenyl, $R^2$ represents hydrogen, hydroxyl or amino, or represents in each case optionally substituted alkyl, alkenyl, alkinyl, alkoxy, alkenyloxy, alkoxycarbonylalkoxy, dialkylaminocarbonylalkoxy, alkylamino, dialkylamino, alkylcarbonylamino, alkoxycarbonylamino, alkylsulphonylamino, aryl, aralkyl, aryloxy, aralkyloxy, arylamino, diarylamino, aralkylamino, N-alkyl-N-arylamino, arylcarbonylamino, heteroarylcarbonylamino or arylsulphonylamino, $R^3$ represents hydrogen, halogen, cyano, carboxyl, alkoxycarbonyl, alkylcarbonylamino or dialkoxyphosphoryl, and $R^4$ represents formyl, cyano, carboxyl, hydroxymethyl or carbamoyl, or represents in each case optionally substituted alkoxycarbonyl, cycloalkoxycarbonyl, alkylthiocarbonyl, alkylaminocarbonyl, cycloalkylaminocarbonyl, dialkylaminocarbonyl, alkylaminocarbonylalkoxycarbonyl, dialkylaminocarbonylalkoxycarbonyl, arylaminocarbonylalkoxycarbonyl, N-alkyl-N-arylaminocarbonylalkoxycarbonyl, pyrrolidinylcarbonyl, piperidinylcarbonyl, morpholinylcarbonyl, piperazinylcarbonyl, aryloxycarbonyl, aralkyloxycarbonyl, heterocyclylalkoxycarbonyl, arylthiocarbonyl, aralkylthiocarbonyl, arylaminocarbonyl, aralkylaminocarbonyl, N-alkyl-N-arylaminocarbonyl, arylhydrazinocarbonyl, alkylhydrazinocarbonyl or phthalimidoxycarbonyl, or $R^4$ together with $R^3$ represents the group —CO—O—$(CH_2)_n$—, n representing the numbers 1 to 4.

The new bisazinyl compounds of the general formula (I) are obtained when (a) hydroxy compounds of the general formula (II)

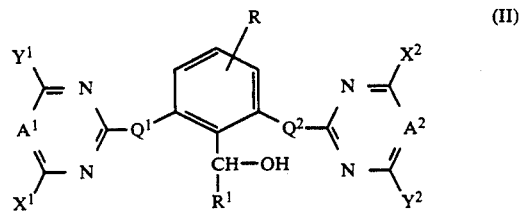

in which $A^1$, $A^2$, $Q^1$, $Q^2$, R, $R^1$, $X^1$, $X^2$, $Y^1$ and $Y^2$ have the abovementioned meaning, are reacted with oxidants ("dehydrating agents"), if appropriate in the presence of diluents, or when (b) benzene derivatives of the general formula (III)

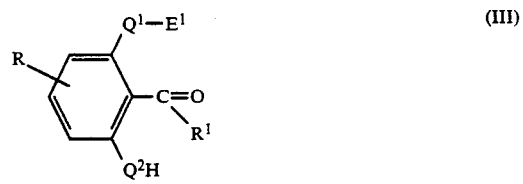

in which $Q^1$, $Q^2$, R and $R^1$ have the abovementioned meaning and $E^1$ represents hydrogen or the group

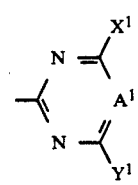

where $A^1$, $X^1$ and $Y^1$ have the abovementioned meaning, are reacted with reactive azines of the general formula (IVa),

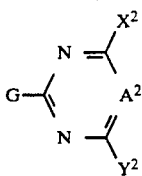

and, if appropriate, also with reactive azines of the general formula (IVb)

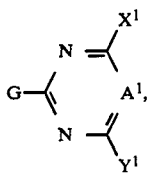

where $A^1$, $A^2$, $X^1$, $X^2$, $Y^1$ and $Y^2$ have the abovementioned meaning and G represents a nucleophilic leaving group, if appropriate in the presence of an acid acceptor and if appropriate in the presence of a diluent, or when (c) carbonyl compounds of the general formula (Ia)

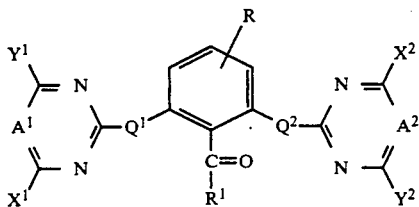

in which $A^1$, $A^2$, $Q^1$, $Q^2$, R, $R^1$, $X^1$, $X^2$, $Y^1$ and $Y^2$ have the abovementioned meaning are reacted with amino compounds of the general formula (V)

in which $R^2$ has the abovementioned meaning, or with methylene compounds of the general formula (VI)

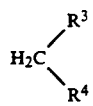

in which $R^3$ and $R^4$ have the abovementioned meaning, if appropriate in the presence of a reaction auxiliary and if appropriate in the presence of a diluent, and, if appropriate, the resulting products of the formula (I) are subsequently converted into other derivatives of the definition of the compounds of the formula (I) using customary methods.

The new bisazinyl compounds of the formula (I) are distinguished by a powerful and selective herbicidal action.

Preferred substituents or ranges of the radicals listed in the formulae mentioned above and below are given in the following text:

Alkyl in the general formulae, alone or in composite radicals such as, for example, alkylamino or alkoxycarbonylalkyl, represents alkyl having preferably 1 to 6, particularly preferably 1 to 4, and especially 1 to 2, carbon atoms. The following may be mentioned by way of example and as being preferred: methyl, ethyl, n- and iso-propyl, and n-, i-, s- and tert.-butyl.

Alkoxy and alkylthio in the general formulae, alone or in composite radicals such as, for example, alkoxycarbonyl or alkylthiocarbonylalkyl, represent alkoxy or alkylthio, each of which has preferably 1 to 6, particularly preferably 1 to 4, and especially preferably 1 to 2, carbon atoms. The following may be mentioned by way of example and as being preferred: methoxy, ethoxy, n- and i-propoxy, n-, i-, s- and tert.-butoxy, methylthio, ethylthio, n- and i-propylthio, and n-, i-, s- and tert.-butylthio.

Alkenyl and alkinyl in the general formulae, alone or in composite radicals, represent alkenyl or alkinyl each of which has preferably 3 to 6, particularly preferably 3 or 4, carbon atoms. The following may be mentioned by way of example and as being preferred: allyl and propargyl.

Halogenoalkyl, halogenoalkoxy and halogenoalkylthio in the general formulae represent straight-chain or branched halogenoalkyl, halogenoalkoxy or halogenoalkylthio, each of which has 1 to 4 and preferably 1 or 2 carbon atoms and in each case 1 to 9 and preferably 1 to 5, identical or different halogen atoms as defined under halogen; the following may be mentioned by way of example and as being preferred: fluoromethyl, chloromethyl, bromomethyl, fluoroethyl, chloroethyl, bromoethyl, fluoro-n-propyl, chloro-n-propyl, dichloromethyl, difluoroethyl, trifluoroethyl, trichloroethyl, trifluorochloroethyl, chlorobutyl, fluorobutyl and especially difluoromethyl, trifluoromethyl, trichloromethyl, dichlorofluoromethyl and chlorodifluoromethyl, and also the halogenoalkoxy radicals or halogenoalkylthio radicals corresponding to these radicals.

The definitions listed here analogously also apply to the preferred combinations of radicals listed in the following text.

The invention preferably relates to compounds of the formula (I) in which $A^1$ and $A^2$ are identical or different and represent nitrogen or a C—X group, X representing hydrogen, halogen, $C_1$-$C_4$-alkyl or $C_1$-$C_4$-alkoxy, $Q^1$ and $Q^2$ are identical or different and represent oxygen, sulphur, NH or N—$C_1$-$C_4$-alkyl, R represents hydrogen, amino, hydroxyl, cyano, nitro, halogen, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-halogenoalkylthio, $C_1$-$C_4$-alkylamino, di-($C_1$-$C_4$-alkyl)-amino, $C_1$-$C_4$-alkylcarbonylamino, $C_1$-$C_4$-alkoxycarbonylamino or $C_1$-$C_4$-alkylsulphonylamino, $X^1$, $X^2$, $Y^1$ and $Y^2$ are identical or different and represent hydrogen, halogen, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-alkylamino or di-($C_1$-$C_4$-alkyl)amino, or represents phenoxy which is optionally substituted by cyano, nitro, halogen, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio and/or $C_1$-$C_4$-alkoxycarbonyl, and Z represents one of the groups below:

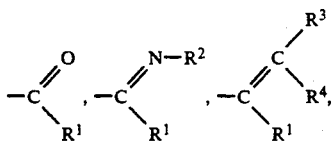

where $R^1$ represents hydrogen, or represents $C_1$–$C_4$-alkyl which is optionally substituted by halogen or $C_1$–$C_2$-alkoxy, or represents phenyl which is optionally substituted by halogen, $C_1$–$C_4$-alkyl and/or $C_1$–$C_4$-alkoxy, $R^2$ represents hydrogen, hydroxyl or amino, or represents $C_1$–$C_6$-alkyl, $C_3$–$C_6$-alkenyl, $C_3$–$C_6$-alkinyl, $C_1$–$C_6$-alkoxy, $C_3$–$C_6$-alkenyloxy, $C_1$–$C_4$-alkoxycarbonyl-$C_1$–$C_2$-alkoxy, di-($C_1$–$C_4$-alkyl)-aminocarbonyl-$C_1$–$C_2$-alkoxy, $C_1$–$C_6$-alkylamino, di-($C_1$–$C_2$-alkyl)-amino, $C_1$–$C_6$-alkylcarbonylamino, $C_1$–$C_6$-alkoxycarbonylamino or $C_1$–$C_6$-alkylsulphonylamino, each of which is optionally substituted by halogen, or represents phenyl, phenyl-$C_1$–$C_4$-alkyl, phenoxy, phenyl-$C_1$–$C_4$-alkoxy, phenylamino, diphenylamino, phenyl-$C_1$–$C_4$-alkylamino, N-($C_1$–$C_4$-alkyl)-N-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxycarbonyl and/or di-($C_1$–$C_2$-alkyl)-amino, $R^3$ represents hydrogen, halogen, cyano, carboxyl, $C_1$–$C_6$-alkoxycarbonyl, $C_1$–$C_6$-alkylcarbonylamino or di-($C_1$–$C_4$-alkoxy)-phosphoryl, and $R^4$ represents formyl, cyano, carboxyl, hydroxymethyl or carbamoyl, or represents $C_1$–$C_6$-alkoxycarbonyl, $C_5$–$C_6$-cycloalkyloxycarbonyl, $C_1$–$C_6$-alkylthiocarbonyl, $C_1$–$C_6$-alkylaminocarbonyl or $C_5$–$C_6$-cycloalkylaminocarbonyl, each of which is optionally substituted by halogen, carboxyl or $C_1$–$C_4$-alkoxycarbonyl, or represents di-($C_1$–$C_2$-alkyl)-aminocarbonyl, or represents $C_1$–$C_4$-alkylamino-carbonyl-$C_1$–$C_4$-alkoxycarbonyl, or represents di-($C_1$–$C_2$-alkyl)-aminocarbonyl-$C_1$–$C_4$-alkoxycarbonyl, or represents phenylaminocarbonyl-$C_1$–$C_4$-alkoxycarbonyl, or represents N-methyl-N-phenylaminocarbonyl-$C_1$–$C_4$-alkoxycarbonyl, or represents pyrrolidinylcarbonyl, piperidinyl-carbonyl, morpholinylcarbonyl or piperazinylcarbonyl, each of which is optionally substituted by methyl and/or ethyl, or represents phenoxycarbonyl, phenyl-$C_1$–$C_4$-alkoxycarbonyl, furylmethoxycarbonyl, thienylmethoxycarbonyl, phenylthiocarbonyl, phenyl-$C_1$–$C_4$-alkylthiocarbonyl, phenylaminocarbonyl, phenyl-$C_1$–$C_4$-alkylamino-carbonyl, N-($C_1$–$C_4$-alkyl)-N-phenylaminocarbonyl or phenylhydrazinocarbonyl or $C_1$–$C_4$-alkylhydrazinocarbonyl, each of which is optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxycarbonyl and/or di-($C_1$–$C_2$-alkyl)amino, or represents phthalimidoxycarbonyl, or together with $R^3$ represents the group —CO—O—(CH$_2$)$_n$—, where n representing the numbers 1 to 4, especially 2 or 3.

The aliphatic hydrocarbon radicals listed in the definition of the compounds according to the invention (for example alkyl, alkenyl or alkinyl), also in combination with hetero atoms (for example in alkoxy, alkylthio or alkylamino) or in compositions such as, for example, halogenoalkyl or halogenoalkoxy, are in each case straight-chain or branched.

Halogen generally represents fluorine, chlorine, bromine or iodine, preferably fluorine, chlorine or bromine, in particular fluorine or chlorine.

The invention especially relates to compounds of the formula (I) in which $A^1$ and $A^2$ are identical or different and represent nitrogen or a C—X group, X representing hydrogen, fluorine, chlorine, bromine, methyl or methoxy, -

$Q^1$ and $Q^2$ are identical or different and represent oxygen, sulphur, NH or N—CH$_3$, R represents hydrogen, amino, hydroxyl, fluorine, chlorine, bromine, methyl, ethyl, trifluoromethyl, methoxy, difluoromethoxy, trifluoromethoxy, methylthio, trifluoromethylthio, methylamino, dimethylamino, acetylamino, methoxycarbonylamino or methylsulphonylamino, $X^1$, $X^2$, $Y^1$ and $Y^2$ are identical or different and represent hydrogen, chlorine, methyl, ethyl, trifluoromethyl, methoxy, ethoxy, difluoromethoxy, methylthio, methylamino, ethylamino or dimethylamino, and Z represents one of the groups below

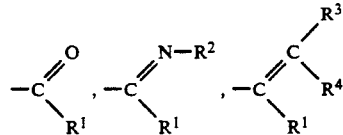

in which $R^1$ represents hydrogen, methyl, ethyl, trifluoromethyl or methoxymethyl, $R^2$ represents hydrogen, hydroxyl, amino, methyl, ethyl, n-propyl, isopropyl, n-butyl, isobutyl, sec-butyl, tert-butyl, allyl, propargyl, methoxy, ethoxy, n-propoxy, isopropoxy, n-butoxy, isobutoxy, sec-butoxy, allyloxy, methoxycarbonylmethoxy, ethoxycarbonylmethoxy, methoxycarbonylethoxy, ethoxycarbonylethoxy, methylamino, ethylamino, n-propylamino, isopropylamino, n-butylamino, isobutylamino, sec-butylamino, tert-butylamino, dimethylamino, acetylamino, propionylamino, methoxycarbonylamino, ethoxycarbonylamino, methylsulphonylamino or ethylsulphonylamino, or represents phenyl, benzyl, phenoxy, benzyloxy, phenylamino, benzylamino, N-methyl-N-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, cyano, fluorine, chlorine, bromine, methyl, trifluoromethyl, methoxy, trifluoromethoxy, methylthio or trifluoromethylthio, $R^3$ represents hydrogen, fluorine, chlorine, cyano, carboxyl, $C_1$–$C_4$-alkoxycarbonyl, $C_1$–$C_4$-alkylcarbonylamino, dimethoxyphosphoryl or diethoxyphosphoryl and $R^4$ represents formyl, cyano, carboxyl, hydroxymethyl or carbamoyl, or represents $C_1$–$C_4$-alkoxycarbonyl, $C_5$–$C_6$-cycloalkyloxycarbonyl, $C_1$–$C_4$-alkylthiocarbonyl, $C_1$–$C_4$-alkylaminocarbonyl or $C_5$–$C_6$-cycloalkylaminocarbonyl, each of which is optionally substituted by fluorine, chlorine, carboxyl or $C_1$–$C_4$-alkoxycarbonyl, or represents dimethylaminocarbonyl, or represents $C_1$–$C_4$-alkylaminocarbonyl-$C_1$–$C_4$-alkoxycarbonyl, or represents dimethylaminocarbonyl-$C_1$–$C_4$-alkoxycarbonyl, or represents N-methyl-N-phenylaminocarbonyl-$C_1$–$C_4$-alkoxycarbonyl, or represents pyrrolidinylcarbonyl, piperidinylcarbonyl, morpholinylcarbonyl or piperazinylcarbonyl, each of which is optionally substituted by methyl and/or ethyl, or represents phenoxycarbonyl, benzyloxycarbonyl, phenylthiocarbonyl, benzylthiocarbonyl, phenylaminocarbonyl, benzylaminocarbonyl, N-methyl-N-phenylaminocarbonyl or phenylhydrazinocarbonyl, each of which is optionally substituted by nitro, cyano, fluorine, chlorine, bromine, methyl, trifluoromethyl, methoxy, trifluoromethoxy, methylthio or trifluoromethylthio, or represents phthalimidoxycarbonyl, or together with $R^6$ represents the group —CO—O—$CH_2CH_2$—.

Very particularly preferred are the compounds of the formula (I) in which $A^1$ and $A^2$ are identical or different and represent nitrogen or a CH group, $Q^1$ and $Q^2$ are identical or different and represent oxygen or sulphur, R represents hydrogen, fluorine or chlorine, $X^1$, $X^2$, $Y^1$ and $Y^2$ are identical or different and represent chlorine, methyl, methoxy or ethoxy, and Z has the meaning mentioned above as being especially preferred.

If, for example, 2,6-bis-(4,6-dimethoxy-s-triazin-2-yl-oxy)-benzyl alcohol and manganese(IV) oxide are used as starting substances in process (a) according to the invention for the preparation of the compounds of the formula (I), the course of the reaction can be illustrated by the following equation:

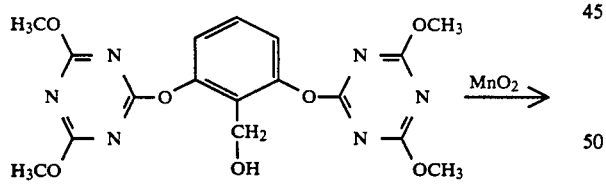

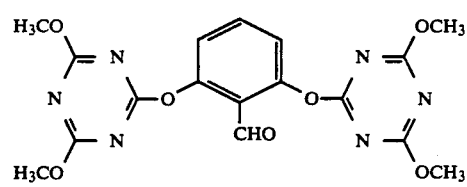

If, for instance, 2-mercapto-6-(4-methoxy-6-methyl-pyrimidin-2-yl-oxy)-benzaldehyde and 2-chloro-4-methoxy-6-methyl-s-triazine are used as starting substances in process (b) according to the invention, the course of the reaction can be illustrated by the following equation:

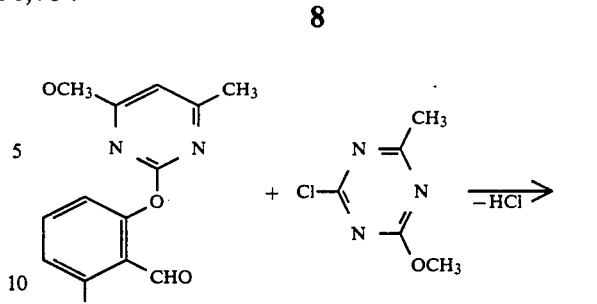

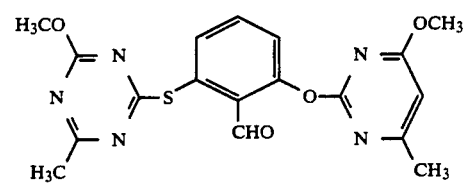

If, for example, 2,6-bis-(4,6-dimethoxy-pyrimidin-2-yl-oxy)-acetophenone and acetohydrazine are used as starting substances in process (c) according to the invention, the course of the reaction can be illustrated by the following equation:

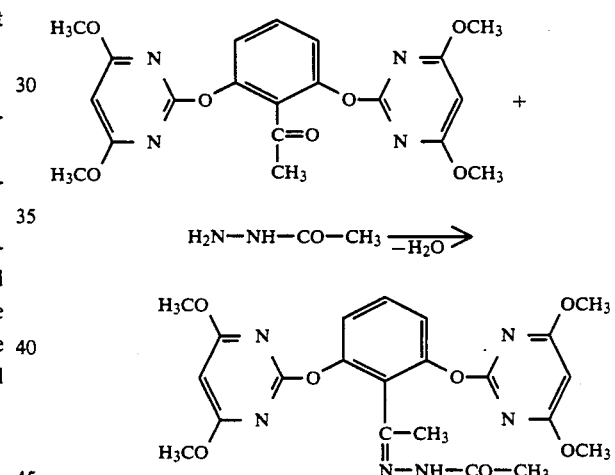

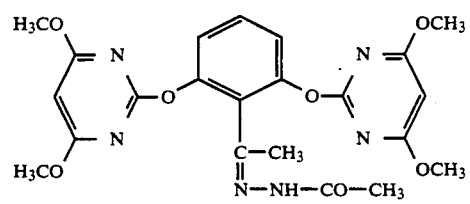

Formula (II) provides a general definition of the hydroxy compounds to be used as starting substances in process (a) according to the invention for the preparation of compounds of the formula (I).

In formula (II), $A^1$, $A^2$, $Q^1$, $Q^2$, R, $R^1$, $X^1$, $X^2$, $Y^1$ and $Y^2$ preferably, or especially, have those meanings which have already been mentioned above in connection with the description of the compounds of the formula (I) according to the invention as being preferred, or especially preferred, for $A^1$, $A^2$, $Q^1$, $Q^2$, R, $R^1$, $X^1$, $X^2$, $Y^1$ and $Y^2$.

The following may be mentioned as examples of the starting substances of the formula (II):

2,6-bis-(4,6-dimethyl-pyrimidin-2-yl-oxy)-, 2,6-bis-(4-methoxy-6-methyl-pyrimidin-2-yl-oxy)-, 2,6-bis-(4,6-dimethoxy-pyrimidin-2-yl-oxy)-, 2,6-bis-(4,6-dimethyl-s-triazin-2-yl-oxy)-, 2,6-bis-(4-methoxy-6-methyl-s-triazin-2-yl-oxy)- and 2,6-bis-(4,6-dimethoxy-s-triazin-2-yl-oxy)benzyl alcohol and -α-methyl-benzyl alcohol.

The hydroxy compounds of the formula (II) were hitherto not known from the literature and are also a subject of the present application.

The new compounds of the formula (II) are obtained when corresponding alkyl compounds of the general formula (VII)

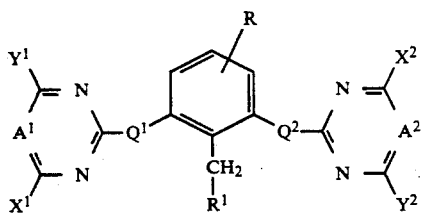

in which $A^1$, $A^2$, $Q^1$, $Q^2$, R, $R^1$, $X^1$, $X^2$, $Y^1$ and $Y^2$ have the above-mentioned meaning are reacted with suitable halogenating agents such as, for example, N-chloro- or N-bromo-succinimide, if appropriate in the presence of a catalyst such as, for example, dibenzoyl peroxide and, if appropriate, in the presence of a diluent such as, for example, tetrachloromethane, at temperatures between 0° C. and 150° C., and the resulting halogenoalkyl compounds of the general formula (VIII)

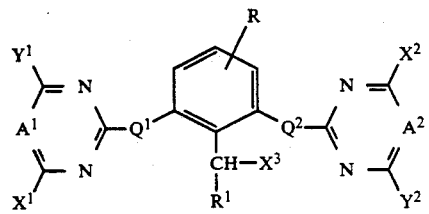

in which $A^1$, $A^2$, $Q^1$, $Q^2$, R, $R^1$, $X^1$, $X^2$, $Y^1$ and $Y^2$ have the above-mentioned meaning and $X^3$ represents chlorine or bromine are reacted with a suitable hydroxylating agent such as, for example, silver nitrate/water, if appropriate in the presence of an organic solvent such as, for example, acetone, at temperatures between 0° C. and 100° C. (cf. the Preparation Examples).

In the formulae (VII) and (VIII), $A^1$, $A^2$, $Q^1$, $Q^2$, R, $R^1$, $X^1$, $X^2$, $Y^1$ and $Y^2$ in each case preferably, or especially, have those meanings which have already been mentioned above in connection with the description of the compounds of the formula (I) according to the invention as being preferred, or especially preferred, for $A^1$, $A^2$, $Q^1$, $Q^2$, R, $R^1$, $X^1$, $X^2$, $Y^1$ and $Y^2$.

The alkyl compounds of the formula (VII) are known and/or can be prepared by processes known per se (cf. EP-A 008,192 and the Preparation Examples).

The halogenoalkyl compounds of the formula (VIII) whose preparation has been described above (cf. also the Preparation Examples) were hitherto not known from the literature and are a subject of the present invention.

Process (a) according to the invention is carried out using oxidants. Oxidants employed for this purpose are preferably the substances customarily used for dehydrating alcohols to give aldehydes or ketones such as, for example, manganese(IV) oxide ("manganese dioxide"), dimethyl sulphoxide/oxalyl chloride (Swern reagent), chromium(VI) oxide or sodium dichromate/sulphuric acid.

Process (a) according to the invention for the preparation of the new bisazinyl compounds of the formula (I) is preferably carried out using diluents. Suitable diluents for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

In process (a) according to the invention, the reaction temperatures can be varied within a substantial range. In general, the process is carried out at temperatures between −80° C. and +150° C., preferably at temperatures between −60° C. and +100° C.

Process (a) according to the invention is generally carried out under atmospheric pressure. However, it is also possible to carry out the process under increased or reduced pressure.

For carrying out process (a) according to the invention, between 1 and 50, preferably between 1 and 25, molar equivalents of the oxidant are generally employed per mole of hydroxy compound of the formula (II).

In general, the starting compound of the formula (II) is initially introduced into a suitable diluent, and the oxidant is slowly added. The reaction mixture is stirred at the temperature required until the reaction is complete and worked up in the customary manner (cf. Preparation Examples).

Formula (III) provides a general definition of the benzene derivatives to be used as starting substances in process (b) according to the invention for the preparation of compounds of the formula (I).

In formula (III), $Q^1$, $Q^2$, R and $R^1$ preferably, or especially, have those meanings which have already been mentioned above in connection with the description of the compounds of the formula (I) according to the invention as being preferred, or as especially preferred, for $Q^1$, $Q^2$, R and $R^1$;

$E^1$ preferably represents hydrogen or the group

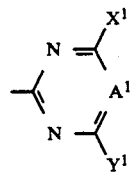

where $A^1$, $X^1$ and $Y^1$ preferably, or especially, have those meanings which have already been mentioned above in connection with the description of the compounds of the formula (I) according to the invention as being preferred, or as especially preferred, for $A^1$, $X^1$ and $Y^1$.

The following may be mentioned as examples of the starting substances of the formula (III): 2-(4,6-dimethylpyrimidin-2-yl-oxy)-, 2-(4-methoxy-6-methyl-pyrimidin-2-yl-oxy)-, 2-(4,6-dimethoxy-pyrimidin-2-yl-oxy)-, 2-(4,6-dimethyl-s-triazin-2-yl-oxy)-, 2-(4-methoxy-6-methyl-s-triazin-2-yl-oxy)- and 2-(4,6-dimethoxy-s-triazin-2-yl-oxy)-6-hydroxy-benzaldehyde and -6-hydroxy-acetophenone, and also 2,6-dihydroxy-benzaldehyde and 2,6-dihydroxy-acetophenone. The benzene derivatives of the formula (III) are known in some cases (cf. JP-A 6,910,256/JP-A 4,410,256—cited in Chem. Abstracts 71, 112633f; J. Med. Chem. 20 (1977), 1194–1199).

The compounds of the formula (IIIa)

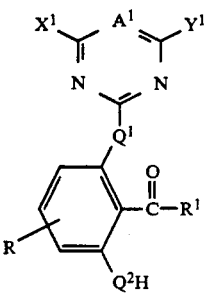

(IIIa)

in which
$A^1$, $Q^1$, $Q^2$, R, $R^1$, $X^1$ and $Y^1$ have the abovementioned meaning
are new and a subject of the present application.

The new compounds of the general formula (IIIa) are obtained when carboxylic acid derivatives of the general formula (IX)

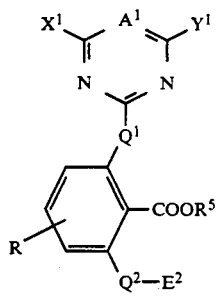

(IX)

in which
$A^1$, $Q^1$, $Q^2$, R, $X^1$ and $Y^1$ have the abovementioned meaning,
$E^2$ represents hydrogen or the group

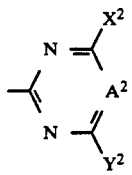

$A^2$, $X^2$ and $Y^2$ having the abovementioned meaning, and
$R^5$ represents hydrogen or lower alkyl,
are reacted with reducing agents such as, for example, sodium borohydride or sodium bis-(2-methoxyethoxy)dihydroaluminate ("Red-Al ®"), if appropriate in the presence of diluents such as, for example, diethyl ether, dimethoxyethane, tetrahydrofuran, toluene, if appropriate also methanol, ethanol or isopropanol, and if appropriate in the presence of a reaction auxiliary such as, for example, N-methyl-piperazine, at temperatures between $-70°$ C. and $+50°$ C., and the mixture is worked up in the customary manner (cf. the Preparation Examples).

In formula (IX), $A^1$, $Q^2$, $Q^2$, R, $X^1$ and $Y^1$ preferably, or especially, have those meanings which have already been mentioned above in connection with the description of the compounds of the formula (I) according to the invention as being preferred, or as especially preferred, for $A^1$, $Q^1$, $Q^2$, R, $X^1$ and $Y^1$; $E^2$ preferably represents hydrogen or the group

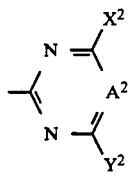

where $A^2$, $X^2$ and $Y^2$ preferably, or especially, have those meanings which have already been mentioned above in connection with the description of the compounds of the formula (I) according to the invention as being preferred, or as especially preferred, for $A^2$, $X^2$ and $Y^2$, and $R^5$ preferably represents hydrogen, methyl or ethyl.

The carboxylic acid derivatives of the formula (IX) are known and/or can be prepared by processes known per se (cf. EP-A 249,708; EP-A 321,846; EP-A 336,494).

Formulae (IVa) and (IVb) provide general definitions of the reactive azines furthermore to be used as starting substances in process (b) according to the invention for the preparation of compounds of the formula (I).

In formulae (IVa) and (IVb), $A^1$, $A^2$, $X^1$, $X^2$, $Y^1$ and $Y^2$ preferably, or especially, have those meanings which have already been mentioned above in connection with the description of the compounds of the formula (I) according to the invention as being preferred, or as especially preferred, for $A^1$, $A^2$, $X^1$, $X^2$, $Y^1$ and $Y^2$, and G preferably represents fluorine, chlorine, bromine or $C_1$–$C_4$-alkylsulphonyl, in particular chlorine or methylsulphonyl.

The following may be mentioned as examples of the starting substances of the formulae (IVa) and (IVb): 2-chloro- and 2-methylsulphonyl-4,6-dimethyl-pyrimidine, -4-methyl-6-methoxy-pyrimidine, -4,6-dimethoxy-pyrimidine, -4-methyl-6-ethoxy-pyrimidine, -4-chloro-6-methoxy-pyrimidine, -4-methyl-pyrimidine, -4-chloro-6-methyl-pyrimidine, -4-trifluoromethyl-6-methoxy-pyrimidine, -4-methoxy-6-difluoromethoxy-pyrimidine, -4-methyl-6-difluoromethoxy-pyrimidine, -4,6-bis-difluoromethoxy-pyrimidine, -4-chloro-6-ethoxy-pyrimidine, -4,6-diethoxy-pyrimidine, -4,5-dichloro-6-methyl-pyrimidine, -4-methyl-5-chloro-6-methoxy-pyrimidine, -4,6-dichloro-pyrimidine, -4-ethyl-6-methoxy-pyrimidine, -5-chloro-4,6-dimethoxy-pyrimidine, -4-methoxy-6-methylamino-pyrimidine and -4,6-bis-trifluoromethyl-pyrimidine and also 2-chloro-4,6-dimethyl-s-triazine, -4-methoxy-6-methyl-s-triazine, -4,6-dimethoxy-s-triazine, -4-ethoxy-6-methyl-s-triazine and -4-ethyl-6-methoxy-s-triazine.

The reactive azines of the formulae (IVa) and (IVb) are known and/or can be prepared by processes known per se (cf. J. Chem. Soc. 1957, 1830, 1833; J. Org. Chem. 26 (1961), 792; U.S. Pat. No. 3,308,119; U.S. Pat. No. 4,711,959).

Process (b) according to the invention is preferably carried out using a diluent. Suitable diluents for this purpose are the same diluents which have been mentioned above in the case of process (a) according to the invention.

Acid acceptors which can be employed in process (b) according to the invention are all acid-binding agents which can customarily be used for reactions of this type. The following are preferably suitable: alkali metal hydrides and alkaline earth metal hydrides such as lithium hydride, sodium hydride, potassium hydride and calcium hydride, alkali metal hydroxides and alkaline earth metal hydroxides such as lithium hydroxide, sodium hydroxide, potassium hydroxide and calcium hydroxide, alkali metal carbonates, alkaline earth metal carbonates, alkali metal hydrogen carbonates and alkaline earth metal hydrogen carbonates such as sodium carbonate, potassium carbonate, sodium hydrogen carbonate and potassium hydrogen carbonate, and also calcium carbonate, or alkali metal acetates such as sodium acetate and potassium acetate, alkali metal alcoholates such as sodium methylate, potassium methylate, sodium ethylate, potassium ethylate, sodium propylate, potassium propylate, sodium isopropylate, potassium isopropylate, sodium butylate, potassium butylate, sodium isobutylate, potassium iso-butylate, sodium tert-butylate and potassium tert-butylate, furthermore basic nitrogen compounds such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

When carrying out process (b) according to the invention, the reaction temperatures can be varied within a substantial range. In general, the process is carried out at temperatures between 0° C. and 150° C., preferably at temperatures between 10° C. and 100° C.

Process (b) according to the invention is generally carried out under atmospheric pressure. However, it is also possible to carry out the process under increased or reduced pressure.

For carrying out process (b) according to the invention, the starting substances required in each case are generally employed in approximately equimolar amounts. However, it is also possible to use one of the two components employed in each case in a larger excess. In general, the reactions are carried out in a suitable diluent in the presence of an acid acceptor, and the reaction mixture is stirred for several hours at the particular temperature required. Working-up in process (b) according to the invention is carried out in each case by customary methods (cf. the Preparation Examples).

Formula (Ia) provides a general definition of the carbonyl compounds to be used as starting substances in process (c) according to the invention for the preparation of compounds of the formula (I).

In formula (Ia), $A^1$, $A^2$, $Q^1$, $Q^2$, R, $R^1$, $X^1$, $X^2$, $Y^1$ and $Y^2$ preferably, or especially, have those meanings which have already been mentioned above in connection with the description of the compounds of the formula (I) according to the invention as being preferred, or as especially preferred, for $A^1$, $A^2$, $Q^1$, $Q^2$, R, $R^1$, $X^1$, $X^2$, $Y^1$ and $Y^2$.

Examples of the starting substances of the formula (Ia) which may be mentioned are: 2,6-bis-(4,6-dimethyl-pyrimidin-2-yl-oxy)-, 2,6-bis-(4,6-dimethoxy-pyrimidin-2-yl-oxy)-, 2,6-bis-(4-methoxy-6-methyl-pyrimidin-2-yl-oxy)-, 2,6-bis-(4,6-dimethyl-s-triazin-2-yl-oxy)-, 2,6-bis-(4,6-dimethoxy-s-triazin-s-yl-oxy)- and 2,6-bis-(4-methoxy-6-methyl-s-triazin-2-yl-oxy)-benzaldehyde and -acetophenone.

The carbonyl compounds of the formula (Ia) are new compounds according to the invention; they can be prepared by processes (a) and (b) according to the invention.

Formulae (V) and (VI) provide general definitions of the amino compounds or methylene compounds furthermore to be used as starting substances in process (c) according to the invention. In these formulae, $R^2$, $R^3$ and $R^4$ preferably, or especially, have the meaning which has already been mentioned above in connection with the description of the compounds of the formula (I) according to the invention as being preferred, or as especially preferred, for $R^2$, $R^3$ and $R^4$.

Examples of the starting substances of the formulae (V) and (VI) which may be mentioned are: ammonia, hydroxylamine, hydrazine, methylamine, ethylamine, propylamine, isopropylamine, butylamine, isobutylamine, sec-butylamine, tert-butylamine, allylamine, propargylamine, O-methyl-, O-ethyl-, O-propyl-, O-isopropyl-, O-butyl-, O-isobutyl- and O-sec-butyl-hydroxylamine, O-allyl-hydroxylamine, methyl aminooxyacetate and ethyl aminooxyacetate, methyl α-aminooxypropionate and ethyl α-aminooxy-propionate, methylhydrazine, ethylhydrazine, propylhydrazine, isopropylhydrazine, butylhydrazine, isobutylhydrazine, sec-butyl-hydrazine, tert-butylhydrazine, N,N-dimethylhydrazine, acetohydrazide, propionyl hydrazide, methoxycarbonylhydrazine, ethoxycarbonylhydrazine, methylsulphonylhydrazine, ethylsulphonylhydrazine, phenylhydrazine, benzoylhydrazine, benzenesulphonylhydrazide, p-toluenesulphonylhydrazide, malonic acid, cyanoacetic acid, malonitrile, methyl cyanoacetate and ethyl cyanoacetate, dimethyl malonate and diethyl malonate, and γ-butyrolactone.

The starting substances of the formula (V) and (VI) are known chemicals for synthesis.

Process (c) according to the invention is preferably carried out using a diluent. The diluents suitable for this purpose are the same as those which have been mentioned above in the case of process (a) according to the invention.

If appropriate, process (c) according to the invention is carried out in the presence of a reaction auxiliary. Suitable reaction auxiliaries are substances which are customarily used for controlling and/or accelerating condensation reactions between carbonyl compounds and amino compounds or methylene compounds. These especially include nitrogen compounds such as, for example, ammonium acetate, β-alanine, pyridine and piperidine.

When carrying out process (c) according to the invention, the reaction temperatures can be varied within a substantial range. In general, the process is carried out at temperatures between 0° C. and 150° C., preferably at temperatures between 10° C. and 120° C.

In general, process (c) according to the invention is carried out under atmospheric pressure. However, it is also possible to carry out the process under increased or reduced pressure.

For carrying out process (c) according to the invention, the starting substances required in each case are generally employed in approximately equimolar amounts. However, it is also possible to use one of the two components employed in each case in a larger excess. In general, the reactions are carried out in a suitable diluent, if appropriate in the presence of a reaction auxiliary, and the reaction mixture is stirred for several hours at the particular temperature required. Working-up in the process according to the invention is carried out in each case by customary methods (compare the Preparation Examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

In particular, the compounds of the formula (I) according to the invention are suitable for combating dicotyledon weeds in monocotyledon cultures such as, for example, wheat, both by the pre-emergence method and the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'- dimethylurea (METABENZTHIAZURON) for combating weeds in cereals; 4-amino-3-methyl-6-phenyl-1,2,4-triazin-5(4H)-one (METAMITRON) for combating weeds in sugar beet, and 4-amino-6-(1,1-dimethylethyl)-3-methylthio-1,2,4-triazin-5(4H)-one (METRIBUZIN) for combating weeds in soya beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-[4-(2,4-dichlorophenoxy)-phenoxy]propionic acid, its methyl ester or its ethyl ester (DICLOFOP); 4-amino-6-t-butyl-3-ethylthio-1,2,4-triazin-5(4H)-one (ETHIOZIN); 2-{4-[(6-chloro-2-benzoxazolyl)oxy-]-phenoxy}-propanoic acid, its methyl ester or its ethyl ester (FENOXAPROP); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N,-(4-isopropylphenyl)urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline (PENDIMETHALIN); 4-ethylamino-2-t-butylamino-6-methylthio-s-triazine (TERBUTRYNE); methyl 3-[[[[4-methoxy-6-methyl-1,3,5-triazin-2-yl)-amino]-carbonyl]-amino]-sulphonyl]-thiophene-2-carboxylate (THIAMETURON); S-(2,3,3-trichloroallyl) N,N-diisopropylthiocarbamate (TRIALLATE).

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

The preparation processes (a) and (b) which have been described above in general give end products of the formula (I) in which Z represents

while process (c) gives end products of the formula (I) in which Z represents

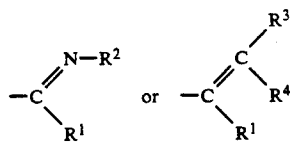

PREPARATION EXAMPLES

Example 1

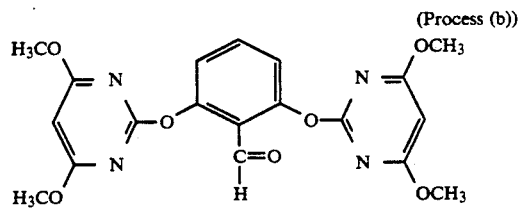

(Process (b))

A mixture of 1.1 g (4 mmol) of 2-(4,6-dimethoxy-pyrimidin-2-yl-oxy)-6-hydroxy-benzaldehyde, 0.9 g (4.2 mmol) of 4,6-dimethoxy-2-methylsulphonyl-pyrimidine, 1.2 g (9 mmol) of potassium carbonate and 40 ml of acetonitrile is refluxed for 5 hours and then concentrated. The residue is taken up in methyl tert-butyl ether, and the mixture is washed twice with water, dried with sodium sulphonate and filtered. The filtrate is evaporated, the residue is triturated with diethyl ether, and the crystalline product is isolated by filtration with suction.

0.9 g (54% of theory) of 2,6-bis-(4,6-dimethoxy-pyrimidin-2-yl-oxy)-benzaldehyde of melting point 129° C. are obtained.

Example 2

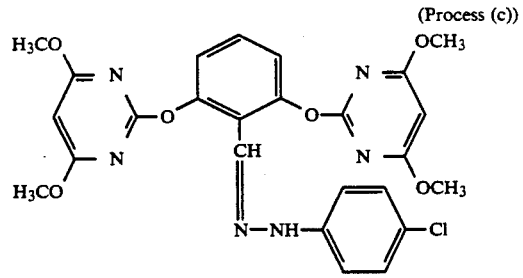

(Process (c))

A mixture of 1.24 g (3 mmol) of 2,6-bis-(4,6-dimethoxypyrimidin-2-yl-oxy)-benzaldehyde, 0.57 g (3.2 mmol) of 4-chloro-phenylhydrazine hydrochloride, 0.3 g (3.7 mmol) of sodium acetate and 60 ml of methylene chloride is stirred for 15 hours at 20° C., and then washed with a 5% strength disodium hydrogen phosphate solution, dried with sodium sulphate and filtered. The filtrate is evaporated, the residue is stirred with hexane, and the crystalline product is isolated by filtration with suction.

1.1 g (68% of theory) of 2,6-bis-(4,6-dimethoxy-pyrimidin-2-yl-oxy)-benzaldehyde 4-(chloro-phenylhydrazone) of melting point 140° C. are obtained.

Other examples of compounds of the formula (1) which can be prepared analogously to Examples 1 and 2 and following the general description of the preparation according to the invention are those listed in Table 1 below.

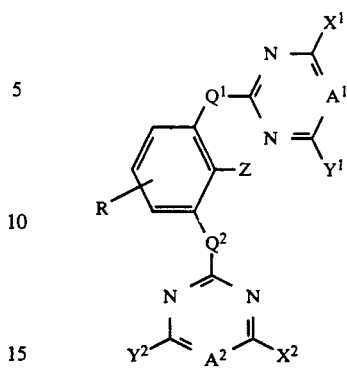
(I)

TABLE 1

Examples of the compounds of the formula (I)

| Ex. No. | $A^1$ | $A^2$ | $Q^1$ | $Q^2$ | R | $X^1$ | $X^2$ | $Y^1$ | $Y^2$ | Z | Melting point (°C.) |
|---|---|---|---|---|---|---|---|---|---|---|---|
| 3 | CH | CH | O | O | H | OCH₃ | OCH₃ | OCH₃ | OCH₃ | —CH=N—NH—C₆H₅ | 115 |
| 4 | CH | CH | O | O | H | OCH₃ | OCH₃ | OCH₃ | OCH₃ | —CH=N—NH—C₆H₄—CH₃ | 121 |
| 5 | CH | CH | O | O | H | OCH₃ | OCH₃ | OCH₃ | OCH₃ | —C(CH₃)=O | 124 |
| 6 | CH | CH | O | O | H | OCH₃ | OCH₃ | OCH₃ | OCH₃ | —C(CH₃)=N—NH—C₆H₅ | 80 |
| 7 | CH | CH | O | O | H | OCH₃ | OCH₃ | OCH₃ | OCH₃ | —CH=N—NH—C₆H₄—NO₂ | 121 |
| 8 | CH | CH | O | O | H | OCH₃ | OCH₃ | OCH₃ | OCH₃ | —CH=N—NH—C₆H₄—CF₃ | 150 |
| 9 | CH | CH | O | O | H | OCH₃ | OCH₃ | OCH₃ | OCH₃ | —CH=N—NH—C₆H₃(Cl)₂ (2,4-diCl) | 168 |
| 10 | CH | CH | O | O | H | OCH₃ | OCH₃ | OCH₃ | OCH₃ | —CH=N—NH—C₆H₄—Cl (2-Cl) | 217 |
| 11 | CH | CH | O | O | H | OCH₃ | OCH₃ | OCH₃ | OCH₃ | —CH=N—NH—C₆H₃(F)₂ (2,4-diF) | 130 |

TABLE 1-continued

Examples of the compounds of the formula (I)

| Ex. No. | A$^1$ | A$^2$ | Q$^1$ | Q$^2$ | R | X$^1$ | X$^2$ | Y$^1$ | Y$^2$ | Z | Melting point (°C.) |
|---|---|---|---|---|---|---|---|---|---|---|---|
| 12 | CH | CH | O | O | H | OCH$_3$ | OCH$_3$ | OCH$_3$ | OCH$_3$ | —CH=N—NH—(4-F-C$_6$H$_4$) | 136 |
| 13 | CH | CH | O | O | H | OCH$_3$ | OCH$_3$ | OCH$_3$ | OCH$_3$ | —CH=N—NH—(3-Cl-C$_6$H$_4$) | 113 |
| 14 | CH | CH | O | O | H | OCH$_3$ | OCH$_3$ | OCH$_3$ | OCH$_3$ | —CH=N—NH—(3-NO$_2$-C$_6$H$_4$) | 165 |
| 15 | CH | CH | O | O | H | OCH$_3$ | OCH$_3$ | OCH$_3$ | OCH$_3$ | —CH=N—NH—(2-pyridyl) | 147 |
| 16 | CH | CH | O | O | H | OCH$_3$ | OCH$_3$ | OCH$_3$ | OCH$_3$ | —CH=N—NH—(3-CH$_3$-C$_6$H$_4$) | 115 |
| 17 | CH | CH | O | O | H | OCH$_3$ | OCH$_3$ | OCH$_3$ | OCH$_3$ | —CH=N—NH—(3-CF$_3$-C$_6$H$_4$) | 115 |
| 18 | CH | CH | O | O | H | OCH$_3$ | OCH$_3$ | OCH$_3$ | OCH$_3$ | —CH=N—NH—(4-C(CH$_3$)$_3$-C$_6$H$_4$) | 123 |
| 19 | CH | CH | O | O | H | OCH$_3$ | OCH$_3$ | OCH$_3$ | OCH$_3$ | —CH=N—NH—(3,4-Cl$_2$-C$_6$H$_3$) | 177 |
| 20 | CH | CH | O | O | H | OCH$_3$ | OCH$_3$ | OCH$_3$ | OCH$_3$ | —CH=N—N(CH$_3$)$_2$ | 85 |
| 21 | CH | CH | O | O | H | OCH$_3$ | OCH$_3$ | OCH$_3$ | OCH$_3$ | —CH=N—NH—(4,6-dimethylpyrimidin-2-yl) | 160 |
| 22 | CH | CH | O | O | H | OCH$_3$ | OCH$_3$ | OCH$_3$ | OCH$_3$ | —CH=N—NH—SO$_2$—CH$_3$ | 171 |
| 23 | CH | CH | O | O | H | OCH$_3$ | OCH$_3$ | OCH$_3$ | OCH$_3$ | —CH=N—NH—SO$_2$—(4-OCH$_3$-C$_6$H$_4$) | (amorphous) |
| 24 | CH | CH | O | O | H | OCH$_3$ | OCH$_3$ | OCH$_3$ | OCH$_3$ | —CH=N—OCH$_3$ | 126 |
| 25 | CH | CH | O | O | H | OCH$_3$ | OCH$_3$ | OCH$_3$ | OCH$_3$ | —CH=N—OH | 157 |

TABLE 1-continued

Examples of the compounds of the formula (I)

| Ex. No. | $A^1$ | $A^2$ | $Q^1$ | $Q^2$ | R | $X^1$ | $X^2$ | $Y^1$ | $Y^2$ | Z | Melting point (°C.) |
|---|---|---|---|---|---|---|---|---|---|---|---|
| 26 | CH | CH | O | O | H | $OCH_3$ | $OCH_3$ | $OCH_3$ | $OCH_3$ | —CH=N—NH—SO$_2$—(2-Cl-phenyl) | 158 |
| 27 | CH | CH | O | O | H | $OCH_3$ | $OCH_3$ | $OCH_3$ | $OCH_3$ | —CH=N—NH—SO$_2$—(2-CF$_3$-phenyl) | 175 |
| 28 | CH | CH | O | O | H | $OCH_3$ | $OCH_3$ | $OCH_3$ | $OCH_3$ | —CH=N—O—CH$_2$—CO—N(C$_3$H$_7$)$_2$ | (amorphous) |
| 29 | CH | CH | O | O | H | $OCH_3$ | $OCH_3$ | $OCH_3$ | $OCH_3$ | —CH=N—N(C$_6$H$_5$)$_2$ | 142 |
| 30 | CH | CH | O | O | H | $OCH_3$ | $OCH_3$ | $OCH_3$ | $OCH_3$ | —CH=N—NH—(4-Br-phenyl) | 148 |
| 31 | CH | CH | O | O | H | $OCH_3$ | $OCH_3$ | $OCH_3$ | $OCH_3$ | —CH=N—NH—(4-CH$_3$,3-Cl-phenyl) | 134 |
| 32 | CH | CH | O | O | H | $OCH_3$ | $OCH_3$ | $OCH_3$ | $OCH_3$ | —CH=N—NH—(3,4-di-CH$_3$-phenyl) | 120 |
| 33 | CH | CH | O | O | H | $OCH_3$ | $OCH_3$ | $OCH_3$ | $OCH_3$ | —CH=N—NH—(4-OCH$_3$-phenyl) | 127 |
| 34 | CH | CH | O | O | H | $OCH_3$ | $OCH_3$ | $OCH_3$ | $OCH_3$ | —CH=N—N(CH$_3$)(phenyl) | 152 |
| 35 | CH | CH | O | O | H | $OCH_3$ | $OCH_3$ | $OCH_3$ | $OCH_3$ | —CH=N—NH—CO—CH$_3$ | 140 |
| 36 | CH | CH | O | O | H | $OCH_3$ | $OCH_3$ | $OCH_3$ | $OCH_3$ | —CH=C(CN)$_2$ | 144 |
| 37 | CH | CH | O | O | H | $OCH_3$ | $OCH_3$ | $OCH_3$ | $OCH_3$ | —CH=N—NH—(3-F-phenyl) | 114 |

STARTING SUBSTANCES OF THE FORMULA (II)

Example (II-1)

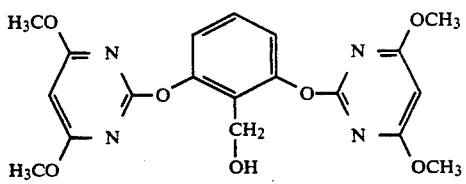

Step 1:

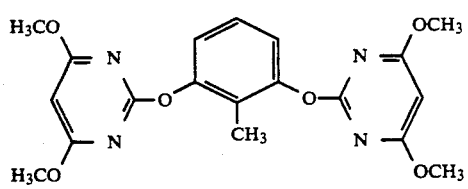

A mixture of 49.7 g (0.4 mol) of 2-methyl-resorcinol, 178.8 g (0.82 mol) of 4,6-dimethoxy-2-methylsulphonyl-pyrimidine, 124.4 g (0.9 mol) of potassium carbonate and 1 liter of acetonitrile is refluxed for 2 days and then concentrated. The residue is stirred with water, and the crystalline product is isolated by filtration with suction (washing with methanol).

135 g (84% of theory) of 2,6-bis-(4,6-dimethoxy-pyrimidin-2-yl-oxy)-toluene of melting point 140° C. are obtained.

Step 2:

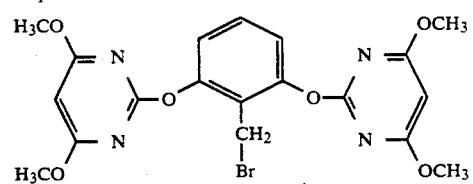

A mixture of 10.0 g (0.025 mol) of 2,6-bis-(4,6-dimethoxy-pyrimidin-2-yl-oxy)-toluene, 4.45 g (0.025 mol) of N-bromo-succinimide, 140 ml of tetrachloromethane and a spatula-tip full of dibenzoyl peroxide is refluxed for 15 hours, then filtered (after cooling), washed twice with water, dried with sodium sulphate and filtered. The filtrate is evaporated, the residue is stirred with petroleum ether, and the crystalline product is isolated by filtration with suction.

9.0 g (75% of theory) of 2,6-bis-(4,6-dimethoxy-pyrimidin-2-yl-oxy)-benzyl bromide of melting point 127° C. are obtained.

Step 3:

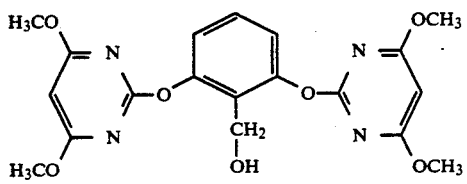

A mixture of 4.8 g (0.01 mol) of 2,6-bis-(4,6-dimethoxypyrimidin-2-yl-oxy)-benzyl bromide, 4.55 g (0.027 mol) of silver nitrate, 40 ml of water and 40 ml of acetone is stirred for 2 hours at 20° C. and then filtered. The filtrate is diluted with ethyl acetate and the organic phase is then separated off, the aqueous phase is re-extracted twice with ethyl acetate; the organic phases are combined, dried with sodium sulphate and filtered. The filtrate is concentrated, and the residue is purified by column chromatography (silica gel; toluene/acetone, 9:1).

1.4 g (34% of theory) of 2,6-bis-(4,6-dimethoxy-pyrimidin-2-yl-oxy)-benzyl alcohol of melting point 122° C. are obtained.

STARTING SUBSTANCES OF THE FORMULA (III)

Example (III-1)

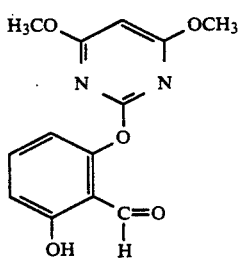

51.6 ml of Red-Al ® (3.4 molar solution of sodium bis-(2-methoxyethoxy)aluminium dihydride—175 mmol—in toluene) are cooled to 0° C. and treated with a solution of 19.3 g (193 mmol) of N-methyl-piperazine in 70 ml of toluene. The mixture is cooled to −60° C., and 23.4 g (53 mmol) of methyl 2,6-bis-(4,6-dimethoxy-pyrimidin-2-yl-oxy)-benzoate in 280 ml of toluene are then added, and the mixture is stirred for 5 hours at −60° C. The mixture is allowed to come to room temperature overnight, water is added, and the mixture is filtered over kieselguhr. The organic phase is removed from the filtrate, the aqueous phase is re-extracted twice with ethyl acetate; the organic phases are combined, dried with sodium sulphate and filtered. The solvent is carefully removed from the filtrate by distillation under a water pump vacuum.

8 g (55% of theory) of 2-(4,6-dimethoxy-pyrimidin-2-yl-oxy)-6-hydroxy-benzaldehyde of melting point 82° C. are obtained.

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction
In this test, a powerful action against weeds is shown, for example, by the compounds of Preparation Examples (1) and (2), while showing good tolerance by crop plants such as, for example, wheat.

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1000 l of water/ha. After three weeks, the degree of damage to the plants is rated in % damage in comparison to the development of the untreated control. The figures denote:
0%=no action (like untreated control)
100%=total destruction In this test, a powerful action against weeds is shown, for example, by the compounds of Preparation Examples (1) and (2), while showing good tolerance by crop plants such as, for example, wheat.

It is understood that the specification and examples are illustrative but not limitative of the present invention and that other embodiments within the spirit and scope of the invention will suggest themselves to those skilled in the art.

What is claimed is:

1. A bisazinyl compound of the formula

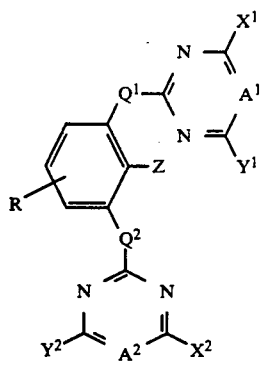

in which
A$^1$ and A$^2$ are identical or different and represent nitrogen or a C—X group, X representing hydrogen, halogen, alkyl or alkoxy,
Q$^1$ and Q$^2$ are identical or different and represent oxygen, sulphur, NH or N-alkyl,
R represents hydrogen, amino, hydroxyl, cyano, nitro, halogen, alkyl, halogenoalkyl, alkoxy, halogenoalkoxy, alkylthio, halogenoalkylthio, alkylamino, dialkylamino, alkylcarbonylamino, alkoxycarbonylamino or alkylsulphonylamino,
X$^1$, X$^2$, Y$^1$ and Y$^2$ are identical or different and represent hydrogen, halogen, alkyl, halogenoalkyl, alkoxy, halogenoalkoxy, alkylthio, alkylamino, dialkylamino or optionally substituted phenoxy, and
Z represents one of the groups below:

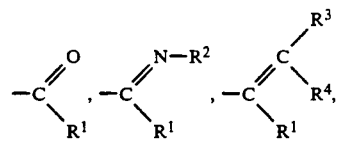

where
R$^1$ represents hydrogen, optionally substituted alkyl or optionally substituted phenyl,
R$^2$ represents hydrogen, hydroxyl or amino, or represents in each case optionally substituted alkyl, alkenyl, alkinyl, alkoxy, alkenyloxy, alkoxycarbonylalkoxy, dialkylaminocarbonylalkoxy, alkylamino, dialkylamino, alkylcarbonylamino, alkoxycarbonylamino, alkylsulphonylamino, aryl, aralkyl, aryloxy, aralkyloxy, arylamino, diarylamino, aralkylamino, N-alkyl-N-arylamino, arylcarbonylamino, heteroarylamino, heteroarylcarbonylamino or arylsulphonylamino,
R$^3$ represents hydrogen, halogen, cyano, carboxyl, alkoxycarbonyl, alkylcarbonylamino or dialkoxyphosphoryl, and
R$^4$ represents formyl, cyano, carboxyl, hydroxymethyl or carbamoyl, or represents in each case optionally substituted alkoxycarbonyl, cycloalkoxycarbonyl, alkylthiocarbonyl, alkylaminocarbonyl, cycloalkylaminocarbonyl, dialkylaminocarbonyl, alkylaminocarbonylalkoxycarbonyl, dialkylaminocarbonylalkoxycarbonyl, arylaminocarbonylalkoxycarbonyl, N-alkyl-N-arylaminocarbonylalkoxycarbonyl, pyrrolidinylcarbonyl, piperidinylcarbonyl, morpholinylcarbonyl, piperazinylcarbonyl, aryloxycarbonyl, aralkyloxycarbonyl, heterocyclylalkoxycarbonyl, arylthiocarbonyl, aralkylthiocarbonyl, arylaminocarbonyl, aralkylaminocarbonyl, N-alkyl-N-arylaminocarbonyl, arylhydrazinocarbonyl, alkylhydrazinocarbonyl or phthalimidoxycarbonyl, or R$^4$ together with R$^3$ represents the group —CO—O—(CH$_2$)$_n$—, n representing the numbers 1 to 4.

2. A bisazinyl compound according to claim 1, in which
A$^1$ and A$^2$ are identical or different and represent nitrogen or a C—X group, X representing hydrogen, halogen, C$_1$-C$_4$-alkyl or C$_1$-C$_4$-alkoxy,
Q$^1$ and Q$^2$ are identical or different and represent oxygen, sulphur, NH or N—C$_1$-C$_4$-alkyl,
R represents hydrogen, amino, hydroxyl, cyano, nitro, halogen, C$_1$-C$_4$-alkyl, C$_1$-C$_4$-halogenoalkyl, C$_1$-C$_4$-alkoxy, C$_1$-C$_4$-halogenoalkoxy, C$_1$-C$_4$-alkylthio, C$_1$-C$_4$-halogenoalkylthio, C$_1$-C$_4$-alkylamino, di-(C$_1$-C$_4$-alkyl)-amino, C$_1$-C$_4$-alkylcarbonylamino, C$_1$-C$_4$-alkoxycarbonylamino or C$_1$-C$_4$-alkylsulphonylamino,
X$^1$, X$^2$, Y$^1$ and Y$^2$ are identical or different and represent hydrogen, halogen, C$_1$-C$_4$-alkyl, C$_1$-C$_4$-halogenoalkyl, C$_1$-C$_4$-alkoxy, C$_1$-C$_4$-halogenoalkoxy, C$_1$-C$_4$-alkylthio, C$_1$-C$_4$-alkylamino or di-(C$_1$-C$_4$-alkyl)amino, or represents phenoxy which is optionally substituted by cyano, nitro, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio and/or $C_1$–$C_4$-alkoxycarbonyl, and Z represents one of the groups below

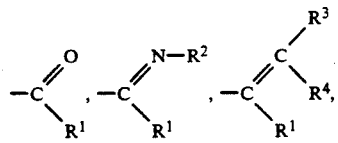

where $R^1$ represents hydrogen, or represents $C_1$–$C_4$-alkyl which is optionally substituted by halogen or $C_1$–$C_2$-alkoxy, or represents phenyl which is optionally substituted by halogen, $C_1$–$C_4$-alkyl and/or $C_1$–$C_4$-alkoxy, $R^2$ represents hydrogen, hydroxyl or amino, or represents $C_1$–$C_6$-alkyl, $C_3$–$C_6$-alkenyl, $C_3$–$C_6$-alkinyl, $C_1$–$C_6$-alkoxy, $C_3$–$C_6$-alkenyloxy, $C_1$–$C_4$-alkoxycarbonyl-$C_1$–$C_2$-alkoxy, di-($C_1$–$C_4$-alkyl)-aminocarbonyl-$C_1$–$C_2$-alkoxy, $C_1$–$C_6$-alkylamino, di-($C_1$–$C_2$-alkyl)-amino, $C_1$–$C_6$-alkylcarbonylamino, $C_1$–$C_6$-alkoxycarbonylamino or $C_1$–$C_6$-alkylsulphonylamino, each of which is optionally substituted by halogen, or represents phenyl, phenyl-$C_1$–$C_4$-alkyl, phenoxy, phenyl-$C_1$–$C_4$-alkoxy, phenylamino, diphenylamino, phenyl-$C_1$–$C_4$-alkylamino, N—($C_1$–$C_4$-alkyl)-N-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxycarbonyl and/or di-($C_1$–$C_2$-alkyl)-amino, $R^3$ represents hydrogen, halogen, cyano, carboxyl, $C_1$–$C_6$-alkoxycarbonyl, $C_1$–$C_6$-alkylcarbonylamino or di-($C_1$–$C_4$-alkoxy)-phosphoryl, and $R^4$ represents formyl, cyano, carboxyl, hydroxymethyl or carbamoyl, or represents $C_1$–$C_6$-alkoxycarbonyl, $C_5$–$C_6$-cycloalkyloxycarbonyl, $C_1$–$C_6$-alkylthiocarbonyl, $C_1$–$C_6$-alkylaminocarbonyl or $C_5$–$C_6$-cycloalkylaminocarbonyl, each of which is optionally substituted by halogen, carboxyl or $C_1$–$C_4$-alkoxycarbonyl, or represents di-($C_1$–$C_2$-alkyl)-aminocarbonyl, or represents $C_1$–$C_4$-alkylamino-carbonyl-$C_1$–$C_4$-alkoxycarbonyl, or represents di-($C_1$–$C_2$-alkyl)-aminocarbonyl-$C_1$–$C_4$-alkoxycarbonyl, or represents phenylaminocarbonyl-$C_1$–$C_4$-alkoxycarbonyl, or represents methyl-N-phenylaminocarbonyl-$C_1$–$C_4$-alkoxycarbonyl, or represents pyrrolidinylcarbonyl, piperidinylcarbonyl, morpholinylcarbonyl or piperazinylcarbonyl, each of which is optionally substituted by methyl and/or ethyl, or represents phenoxycarbonyl, phenyl-$C_1$–$C_4$-alkoxycarbonyl, furylmethoxycarbonyl, thienylmethoxycarbonyl, phenylthiocarbonyl, phenyl-$C_1$–$C_4$-alkylthiocarbonyl, phenylaminocarbonyl, phenyl-$C_1$–$C_4$-alkylaminocarbonyl, N-($C_1$–$C_4$-alkyl)-N-phenylamino-carbonyl or phenylhydrazinocarbonyl or $C_1$–$C_4$-alkylhydrazinocarbonyl, each of which is optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxycarbonyl and/or di-($C_1$–$C_2$-alkyl)amino, or represents phthalimidoxycarbonyl, or together with $R^3$ represents the group —CO—O—($CH_2$)$_n$—, n representing the numbers 1 to 4, especially 2 or 3.

3. A compound according to claim 1, wherein such compound is 2,6-bis-(4,6-dimethoxy-pyrimidin-2-yl-oxy)-benzaldehyde of the formula

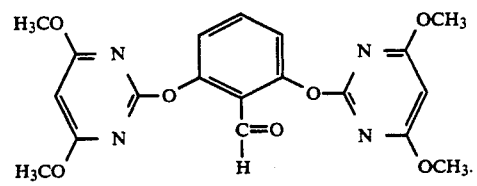

4. A compound according to claim 1, wherein such compound is 2,6-bis-(4,6-dimethoxy-pyrimidin-2-yl-oxy)-benzaldehyde 4-(chloro-phenylhydrazone) of the formula

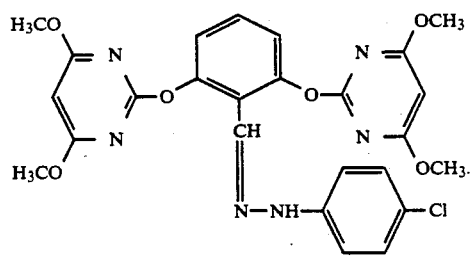

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is
2,6-bis-(4,6-dimethoxy-pyrimidin-2-yl-oxy)-benzaldehyde, or
2,6-bis-(4,6-dimethoxy-pyrimidin-2-yl-oxy)-benzaldehyde 4-(chloro-phenylhydrazone).

8. A hydroxy compound of the formula (II)

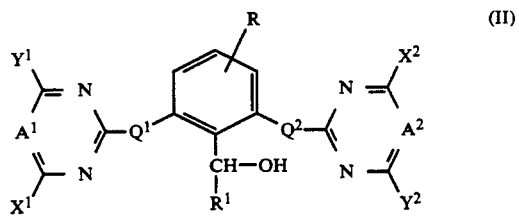

in which
$A^1$ and $A^2$ are identical or different and represent nitrogen or a C—X group, X representing hydrogen, halogen, alkyl or alkoxy,
$Q^1$ and $Q^2$ are identical or different and represent oxygen, sulphur, NH or N-alkyl, R represents hydrogen, amino, hydroxyl, cyano, nitro, halogen, alkyl, halogenoalkyl, alkoxy, halogenoalkoxy, alkylthio, halogenoalkylthio, alkylamino, dialkylamino, alkylcarbonylamino, alkoxycarbonylamino or alkylsulphonylamino, $X^1$, $X^2$, $Y^1$ and $Y^2$ are identical or different and represent hydrogen, halogen, alkyl, halogenoalkyl, alkoxy, halogenoalkoxy, alkylthio, alkylamino or dialkylamino, or represent optionally substituted phenoxy, and $R^1$ represents hydrogen, or represents optionally substituted alkyl, or represents optionally substituted phenyl.

9. A halogenoalkyl compound of the formula

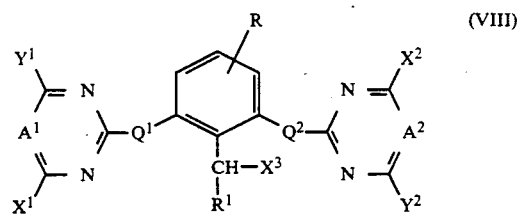

(VIII)

in which
$A^1$ and $A^2$ are identical or different and represent nitrogen or a C—X group, X representing hydrogen, halogen, alkyl or alkoxy, $Q^1$ and $Q^2$ are identical or different and represent oxygen, sulphur, NH or N-alkyl, R represents hydrogen, amino, hydroxyl, cyano, nitro, halogen, alkyl, halogenoalkyl, alkoxy, halogenoalkoxy, alkylthio, halogenoalkylthio, alkylamino, dialkylamino, alkylcarbonylamino, alkoxycarbonylamino or alkylsulphonylamino, $X^1$, $X^2$, $Y^1$ and $Y^2$ are identical or different and represent hydrogen, halogen, alkyl, halogenoalkyl, alkoxy, halogenoalkoxy, alkylthio, alkylamino or dialkylamino, or represent optionally substituted phenoxy, $R^1$ represents hydrogen, or represents optionally substituted alkyl, or represents optionally substituted phenyl, and $X^3$ represents chlorine or bromine.

* * * * *